United States Patent [19]

Kimura et al.

[11] 4,247,415
[45] Jan. 27, 1981

[54] RUST INHIBITORS AND COMPOSITIONS OF SAME

[75] Inventors: Shoji Kimura, Chigasaki; Noboru Ishida, Sagamihara, both of Japan

[73] Assignee: Nippon Oil Company, Ltd., Tokyo, Japan

[21] Appl. No.: 73,853

[22] Filed: Sep. 10, 1979

Related U.S. Application Data

[62] Division of Ser. No. 958,631, Nov. 8, 1978, abandoned.

[30] Foreign Application Priority Data

Nov. 30, 1977 [JP] Japan .................. 52/142600

[51] Int. Cl.$^3$ .......................................... C23F 11/12
[52] U.S. Cl. .............................. 252/396; 106/14.22;
  106/14.26; 422/12; 568/648
[58] Field of Search ................. 252/396; 106/14.22,
  106/14.26; 422/12; 568/648

[56] References Cited

U.S. PATENT DOCUMENTS

| | | | |
|---|---|---|---|
| 2,075,018 | 3/1937 | Bruson et al. | 568/648 |
| 2,166,518 | 7/1939 | Caplan | 568/648 |
| 2,434,797 | 1/1948 | Harvey | 568/648 |
| 2,486,925 | 11/1949 | Carroll | 568/648 |

FOREIGN PATENT DOCUMENTS 36-8926  6/1961  Japan .

Primary Examiner—Benjamin R. Padgett
Assistant Examiner—Irwin Gluck

[57] ABSTRACT

There is disclosed a rust inhibitor consisting of glycerol alkyl phenylether of the formula

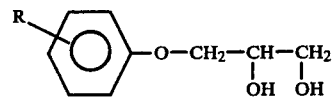

wherein R is an alkyl group of $C_{6-18}$.

A composition having rust preventing result may be obtained by adding the rust inhibitor to a mineral oil.

4 Claims, No Drawings

RUST INHIBITORS AND COMPOSITIONS OF SAME

This is a division of application Ser. No. 958,631 filed Nov. 8, 1978 now abandoned.

BACKGROUND OF THE INVENTION

Hitherto, there can be found two kinds of uses in rust inhibitors, one is the use of same to provide rust preventing property to a lubricant such as turbine oil, engine oil, gear oil or hydraulic fluid and the other is the use of same as an ingredient in so-called rust preventive oils which prevent rusting of metallic products.

Primary properties required in these inhibitors are to have enough solubility to a mineral oil used and to adsorb to a metal surface strongly to prevent water, salts, corrosive gases (NOx, SOx) and dust from attacking chemically on metal surface which cause rusting.

In the past, organic carboxylic acids, a salt or an ester thereof, sulfonates, amines, phosphoric acid, salts or esters thereof have been well-known as a rust inhibitor. As an industrial lubricant organocarboxylic acids, especially alkenyl succinic acid and esters thereof have been primarily used. And as a rust preventing agent, organocarboxylic acid esters have typically been used.

The alkenyl succinic acid and its derivatives have been apt to interfere with the operation of machines due to the fact that corrosion could occur to effect precipitates and/or adhesive substances by their strong acidic carboxyl groups when they are brought into contact with non-ferrous metals, for example, copper-tin alloy, copper-zinc alloy and the like.

The organocarboxylic acid esters have a similar drawback by the fact that their ester bonds used to be cleaved by their hydrolysis due to moisture and heat derived from their environment to isolate carboxyl groups.

Further, these rust inhibitors also have such a drawback that they often form precipitates and/or sludges by a chemical reaction when they are brought into contact with basic substances thereby becoming the origin of a trouble in the case of being used jointly with basic additives or in the case of being used in ammonia compressor lubricants.

On the other hand, the organocarboxylic acid esters also form an acid by the hydrolysis of their ester bonds as mentioned above and the acid causes discoloring of a metal surface. In addition to the above noted, they had lower demulsibility.

Inventors of the present invention arrived at the present invention as a result of serious efforts for developing a rust inhibitor not having the aforementioned drawbacks.

It has been well-known that an organic compound having polar groups is useful as a rust inhibitor.

In order to avoid the above drawbacks, two chemically neutral hydroxy groups, selected as polar groups, are combined with an oleophilic group of the rust inhibitor through an ether bond.

SUMMARY OF THE INVENTION

An object of the present invention, therefore, is to provide a rust inhibitor not having the drawbacks usually encountered in conventional rust inhibitors, which consists of glycerol alkyl phenyl ether of the formula

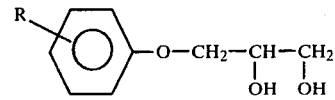

wherein R is an alkyl group of $C_{6-18}$.

Another object of the present invention is to provide a composition having superior rust preventing ability.

A further object of the invention is to provide a composition obtained by adding the aforesaid rust inhibitor to a mineral oil.

DETAILED DESCRIPTION OF THE INVENTION

Glycerol alkylphenyl ether according to the present invention may be prepared by, for example, hydration of alkylphenylglycidyl ether or by heating alkylphenol and glycerol-α-monochlorohydrin in the presence of sodium hydroxide.

The number of carbon atoms of the alkyl group substituted for the phenyl group of the above ether is 6-18. The alkyl group is preferably in the sequence of nonyl, dodecyl, pentadecyl, hexyl and octadecyl, and the most preferable alkyl group is nonyl group of $C_9$.

In the case where the carbon number of the alkyl group is less than 6, solubility of the glycerol ether obtained to a mineral oil is so poor that a composition containing the ether and mineral oil has no practical use. On the contrary, glycerol alkylphenyl ether having an alkyl group of more than 18 carbon atoms has better solubility but is poor in rust inhibitability.

The carbon number used heretofore refers to the carbon number of a primary ingredient and a small amount of alkyl groups having a different carbon number may be present.

The alkyl groups may be located at any position, for example, at o, m, or p position of the benzene nucleus, but it is preferable that the alkyl group is present at the p-position.

The mineral oil heretofore referred to in the present specification is the one generally used as a base oil of a lubricant or a rust inhibitive oil, for example, lubricant fraction of naphthenic or paraffin oils having 20–150 cSt. of viscosity at 37.8° C., refined products thereof, petroleum solvents, petrolatum and the like.

The aforesaid glycerol alkylphenyl ether is added to a mineral oil to produce lubricants or rust preventive oils.

The amount of the rust inhibitor to be added to a mineral oil is in the range of 0.01–20 wt. parts based on 100 parts by weight of the mineral oil. In the case where the amount of a rust inhibitor used is less than 0.01 wt. parts per 100 wt. parts of a mineral oil, rust preventing effect obtained is poor and in the case of using more than 20 wt. parts per 100 wt. parts of a mineral oil, sufficient rust preventing effect corresponding to the amount of the rust inhibitor used may not be obtained and such use is commercially unsuitable.

The addition amount of the rust inhibitor for preparing a lubricant is in the range of 0.01–1.0 wt. parts bases on 100 wt. parts of the mineral oil used, preferably 0.03–0.50 wt. parts. And the one for preparing a rust preventive oil is in the range of 0.1–20 wt. parts per 100 wt. parts of the mineral oil, preferably 0.5–5 wt. parts.

It is also possible to use another additives jointly with the aforesaid ether in the case of producing a lubricant or a rust preventive oil. In such a case, both acidic and basic materials may be incorporated as additives.

The following is an example for preparing rust inhibitors according to the present invention.

PREPARATION EXAMPLE

Into a 500 ml. flask were put 110 g (0.5 mol) of p-nonylphenol and 110.5 g (1 mol) of glycerol-α-monochlorohydrin and the mixture was gradually heated in the presence of 24 g (0.6 mol) of sodium hydroxyde in nitrogen atmosphere to react them for 5 hours at 100° C. Then, the reactants were cooled.

Following the extraction of the resulting product with 1 liter of ethylether, the extract was washed with water and distilled for 3 hours at 170° C./1 mmHg to remove unreacted substances and water, giving 120.4 g of transparent glycerol-p-nonylphenyl ether.

In the same manner as described above, glycerol alkylphenyl ethers of $C_{10-18}$ could be obtained.

The resulting ethers were evaluated by the following performance tests on the basis of the Japanese Industrial Standard as shown below.

JIS K. 2510; Test method for rust-preventing characteristics of turbine oils Into a mixture of a sample and water, a test piece of iron is immersed and the mixture is stirred for 24 hours at 60° C. Thereafter, the presence or absence of rusting on the surface of the test piece is investigated.

JIS K 2517; Test method for steam emulsion number of lubricating oils

Steam is blown into a sample until the total volume of the sample and condensed water becomes 52–55 ml and then the separated state of the sample and condensed water is observed. The demulsibility is determined as a number of seconds required by the time where the separation amount of the oil phase becomes 20 ml. It is regarded as "above 1200 seconds" if the amount of the separated oil does not reach 20 ml. after 20 minutes.

JIS K 2515; Test method for oxidation characteristics of turbine oils

Oxygen is blown into a sample at 95° C. in the presence of steel wire; copper wire and water to observe surface changes of the metals and the state of water and oil phases.

JIS Z 0236; Test method for rust preventive oils

A test piece of steel, coated with a sample, is hund in a humidity cabinet and rotated for 200 hours at 49 1° C. in above 95% relative humidity.

Thereafter, the degree of rusting on the test piece is measured to evaluate same with "A(superior) - E(inferior)".

JIS K 2520; Test method for emulsion characteristics of lubricating oils

A sample is mixed with water and kept at 54 1° C. with stirring to observe the state, separated into water and oil phase, of the resulting emulsion.

The evaluation of the state is shown as; Oil phase (ml)—Water phase (ml)—emulsion phase [time passed (min.)]

The present invention will be further illustrated in more detail by way of the following examples and controls.

EXAMPLES 1–5 AND CONTROL 1

The lubricants used in examples 1–5 were prepared by respectively adding glycerol-p-hexylphenyl ether, glycerol-p-nonylphenyl ether, glycerol-p-pentadecylphenyl ether, glycerol-p-dodecylphenyl ether and glycerol-p-octadecylphenyl ether made according to the manner described in the foregoing Preparation Example to a purified lubricant fraction, obtained from the Minas crude oil, having the viscosity of 56 cST. at 37.8° C. and the lubricant used in the Control 1 was prepared by adding commercially available 2-oxypropyl-2'-alkenyl-monosuccinate of the formula

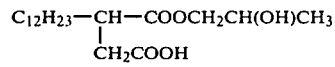

as a rust inhibitor to the above lubricant fraction.

The results of the test for steam emulsion number of lubricating oils and the test for rust-preventing characteristics of the turbine oils carried out with the above lubricants are shown in Table 1.

TABLE 1

| | Lubricant composition (parts by weight) | | Test Result | |
| --- | --- | --- | --- | --- |
| | Mineral oil | Rust inhibitor | Test for rust preventing characteristics of turbine oils | Test for steam emulsion number of lubricating oil |
| Example 1 | lubricant fraction obtained from Minas crude oil (100) | glycerol-p-hexylphenyl ether (0.10) | pass | 110 |
| 2 | same as above | glycerol-p-nonylphenyl ether (0.10) | pass | 93 |
| 3 | same as above | glycerol-p-pentadecylphenyl ether (0.10) | pass | 105 |
| 4 | same as above | glycerol-p-dodecylphenyl ether (0.10) | pass | 100 |
| 5 | same as above | glycerol-p-octadecylphenyl ether (0.10) | pass | 120 |
| Control 1 | same as above | alkenyl monosuccinate (0.10) | pass | above 1200 |

The compositions used in Examples 1–5 had excellent performance in each test. On the contrary, the composition used in Control 1 stood the test for rust preventing characteristics of turbine oils but showed unfavorable results in the test for steam emulsion number of lubricating oils. It seems that the unfavorable results are due to the hydrolysis of the ester bonds contained in the alkenyl monosuccinate.

EXAMPLES 6–10 AND CONTROL 2

The lubricants used in Examples 6–10 were prepared with glycerol-p-hexylphenyl ether, glycerol-p-nonylphenyl ether, glycerol-p-pentadecylphenyl ether, glycerol-p-dodecylphenyl ether and glycerol-p-octadecylphenyl ether made according to the Preparation Example by adding these ethers to the same lubricant fraction as used in Example 1–5 and that used in control 2 was prepared with the commercially available alkenyl monosuccinate used in Control 1 in the same manner as in Examples 6–10.

Using these lubricants, test for oxidation characteristics of turbine oils was carried out. The results obtained are shown in Table 2.

EXAMPLES 11–15 AND CONTROL 3

In Examples 11–15 and Control 3, rust preventive oils made with glycerol alkylphenyl ethers prepared according to the foregoing Preparation Example and made with commercially available sorbitan mono-oleate as a control were used to carry out the test for rust preventive oils and the test for emulsion characteristics of lubricating oils. The results obtained are shown in Table 3.

TABLE 3

| | Rust preventing oil composition (parts by weight) | | Test for rust preventive oils | Test for emulsion characteristics of lubricating oils |
|---|---|---|---|---|
| | Mineral oil | Rust inhibitor | | |
| Example 11 | Purified spindle oil obtained from Arabian crude oil (100) | glycerol-p-nonylphenyl ether (0.50) | A | 40-40-0 (5) |
| 12 | same as above (100) | glycerol-p-dodecylphenyl ether (0.50) | A | 40-40-0 (7) |
| 13 | same as above (100) | glycerol-p-pentadecylphenyl ether (0.50) | A | 40-40-0 (7) |
| 14 | same as above (100) | glycerol-p-hexylphenyl ether (0.50) | A | 40-40-0 (9) |
| 15 | same as above (100) | glycerol-p-octadecylphenyl ether (0.50) | A | 40-40-0 (9) |
| Control 3 | same as above (100) | sorbitan monooleate (0.50) | A | 41-38-1 (10) |

As will be seen from Table 3, with the compositions made according to the present invention, there can scarcely be found an emulsified layer and they are excellent in demulsibility as compared with that of a conventional rust preventive oil and shows excellent performance as a rust preventive oil.

What we claim is:

TABLE 2

| | Lubricant Composition (parts by wt.) | | | Test for oxidation characteristics of turbine oils | | | |
|---|---|---|---|---|---|---|---|
| | Mineral oil | Rust inhibitor | Other additive | oil phase | water phase | iron surface | copper surface |
| Example 6 | Lubricant fraction obtained from Minas crude oil (100) | glycerol-p-hexylphenyl ether (0.10) | 2.6-ditert.Bu-p-cresol (0.60) | transparent | transparent | lustrous | lustrous |
| 7 | same as above | glycerol-p-nonylphenyl ether (0.10) | same as above | same as above | same as above | same as above | same as above |
| 8 | same as above | glycerol-p-pentadecylphenyl ether (0.10) | same as above | same as above | same as above | same as above | same as above |
| 9 | same as above | glycerol-p-dodecylphenyl ether (0.10) | same as above | same as above | same as above | same as above | same as above |
| 10 | same as above | glycerol-p-octadecylphenyl ether (0.10) | same as above | same as above | same as above | same as above | same as above |
| Control 2 | same as above | alkenyl monosuccinate (0.10) | same as above | rather whity turbid | rather whity turbid | grayish | darkened |

As will be seen from Table 2, there was found no deterioration of oil in the compositions according to the present invention and surfaces of metal pieces used as a catalyst were also clean. On the contrary, the composition used in Control 2 had whity turbid water phase and oil phase. This seems to have been derived from the hydrolysis of the rust inhibitor used in Control 2. Further, in case of the Control 2, the surfaces of the metals used were lusterless. This seems to be due to the chemical reaction of the rust inhibitor used in the Control 2 with the surfaces of the metals used.

1. A composition having rust preventing ability which comprises (A) a glycerol-p-alkylphenyl ether of the formula

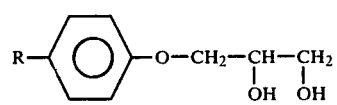

wherein R is an alkyl radical with 9 or 12 carbon atoms and (B) a mineral oil in a weight ratio of 0.01–20 parts of (A) per 100 parts of (B).

2. A composition according to claim 1, wherein said glycerol alkylphenyl ether is selected from the group consisting of glycerol-p-nonylphenyl ether and glycerol-p-dodecylphenyl ether.

3. A method of inhibiting rust formation on metallic surfaces, which comprises admixing (A) glycerol-p-alkylphenyl ether of the formula

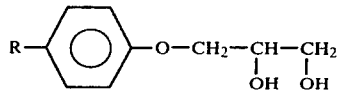

wherein R is an alkyl radical with 9, or 12 carbon atoms, with (B) a mineral oil, in a weight ratio of 0.01–20 parts of (A) per 100 parts of (B); and applying the resulting admixture to a metal surface, whereby rusting is inhibited.

4. The method according to claim 3, wherein said glycerol-p-alkylphenyl ether is selected from the group consisting of glycerol-p-nonylphenyl ether and glycerol-p-dodecylphenyl ether.

* * * * *